United States Patent [19]

Walser

[11] 4,100,161
[45] Jul. 11, 1978

[54] PROMOTION OF PROTEIN SYNTHESIS AND SUPPRESSION OF UREA FORMATION IN THE BODY BY KETO ANALOGS OF ESSENTIAL AMINO ACIDS

[75] Inventor: Mackenzie Walser, Ruxton, Md.

[73] Assignee: The Johns Hopkins University, Baltimore, Md.

[21] Appl. No.: 669,590

[22] Filed: Mar. 23, 1976

Related U.S. Application Data

[63] Continuation-in-part of Ser. No. 461,222, Apr. 15, 1974, abandoned, which is a continuation-in-part of Ser. No. 355,327, Apr. 30, 1973, abandoned, which is a continuation-in-part of Ser. No. 270,986, Jul. 12, 1972, abandoned.

[51] Int. Cl.² ............... A61K 31/40; A61K 31/19; A61K 31/195
[52] U.S. Cl. ................................ 424/274; 424/317; 424/319
[58] Field of Search ............... 424/274, 319, 317

[56] References Cited

U.S. PATENT DOCUMENTS

| | | | |
|---|---|---|---|
| 2,457,820 | 1/1949 | Howe et al. | 424/319 |
| 3,764,703 | 10/1973 | Bergström et al. | 424/319 |

OTHER PUBLICATIONS

Chemical Abstracts 81:54452q (1974).
Chemical Abstracts 82:144958j (1975).
Richards et al., Lancet pp. 128-134 (7-17-71).
Richards et al., Lancet pp. 841-849 (10-21-67).
Rudman J. of Clinical Invest. 50, pp. 90-96, (1971).

Primary Examiner—Leonard Schenkman
Attorney, Agent, or Firm—Seidel, Gonda & Goldhammer

[57] ABSTRACT

Compositions containing the keto analogs of certain of the amino acids essential for humans are therapeutically employed in the treatment of patients confined to low or restricted protein diet, particularly in cases of renal diseases. These analogs promote protein synthesis in the human body and suppress undesired urea formation, partly as a result of altering the body's mechanisms for conserving protein.

18 Claims, 6 Drawing Figures

PROMOTION OF PROTEIN SYNTHESIS AND SUPPRESSION OF UREA FORMATION IN THE BODY BY KETO ANALOGS OF ESSENTIAL AMINO ACIDS

STATEMENT OF GOVERNMENT INTEREST

The invention described herein was made in the course of work under a grant or award from the Department of Health, Education and Welfare.

CROSS-REFERENCE TO RELATED APPLICATIONS

This application is a continuation-in-part of U.S. application Ser. No. 461,222 (now abandoned) entitled "Composition and Method for Promotion of Protein Synthesis and Suppression of Urea Formation in the Body", filed Apr. 15, 1974; which application Ser. No. 461,222 is a continuation-in-part of U.S. Pat. application Ser. No. 355,327 (now abandoned) having the same title and was filed Apr. 30, 1973 as a continuation-in-part of U.S. patent application Ser. No. 270,986 (now abandoned) entitled "Composition and Method of Treating Uremia", filed July 12, 1972.

BACKGROUND OF THE INVENTION

A. Field of the Invention

The invention generally relates to a therapeutic composition of matter and method for administering said composition to human beings. Particularly, the several embodiments of the invention provide for treatment of renal disorders, such as uremia for alleviating the effects of tissue wasting disorders characterized by protein deficiency and for altering metabolic pathways in order to prevent leakage of nitrogen from the body's metabolic pool.

B. Description of the Prior Art

Prior art treatment of the several bodily disorders to which the present invention finds application varies according to the particular disorder, this variation resulting in certain instances from a lack of understanding of the metabolic processes involved in the respective situations. Other than dialysis, prior art treatments applicable to renal disorders, such as uremia, center around replacement of amino acids lacking in the individual suffering from said disorder. In a situation of this nature, nitrogenous wastes resulting from the normal breakdown of amino acids in the body are not adequately excreted and accumulate in the blood. Due to the inability to excrete these wastes, ingestion of protein must be restricted, thereby resulting in amino acid deficiencies. One particular treatment disclosed by Howe et al. in U.S. Pat. No. 2,457,820 provides for administering certain essential amino acids to correct this protein deficiency without overburdening the remaining kidney function.

Bergstrom et al. in U.S. Pat. No. 3,764,703 discloses a mixture of eight essential amino acids optionally combined with either or both L-arginine and L-histidine (which the patent calls "semi-essential" amino acids) for treatment of uremic conditions caused by renal insufficiency. However, the provision of additional amino acids in the blood stream often results in overburdenment of the kidney function, especially in severe cases, due to the resulting breakdown of the introduced amino acids into excessive nitrogenous wastes. Furthermore, these compounds are highly unpleasant to taste. For a comparison of results of essential amino acids therapy as opposed to that employing essentially the compositions of the present invention, see Walser et al. (1973), *Journal of Clinical Investigation*, 52:679. Also, Walser, M., (1975) "Keto-acids in the Treatment of Uremia", *Clinical Nephrology*, 3:80.

Other workers studying renal failure have suggested the dietary use of keto-acid analogs of amino acids and have proposed but have not demonstrated the use of keto-analogs of a combination of certain essential amino acids as a therapeutically beneficial treatment for uremia. These prior suggestions have been based on the assumption that such keto-acid analogs might combine with nitrogen derived from urea breakdown in the intestines. Subsequently, such suggestions relating to keto-acid usage have been discounted. See editorial in *The Lancet*, Aug. 2, 1975, page 214. The work resulting in the present invention has demonstrated the actual therapeutic value of keto-acid usage and has proven the prior assumptions to be inaccurate. In particular, urea breakdown in renal disorders does not produce an excess of nitrogen in the body. To the contrary, the amount of urea breakdown in the body in renal failure is normal. Thus, an excess of nitrogen is not available to aminate keto-acids and, even if urea breakdown is reduced to zero, the therapeutic use of keto-acids proves effective. The present teachings are thus based on heretofore unobvious understandings of the body's metabolic processes. Nitrogen is diverted away from urea formation, this nitrogen now being known to derive from body metabolic processes themselves. A particular object of the invention can then be seen to be the suppression of urea formation. Urea breakdown in the intestines is accordingly minimized.

Prior art treatment of hepatic failure, such as is characterized by hyperammonemia and portal-systemic encephalopathy, is generally based on attempts to reduce the production of ammonia in the intestines and to restrict dietary protein. Antibiotics are usually applied to prevent urea breakdown. And so, according to prior teachings, the use of keto-acids to alleviate heptatic failure would have been considered ineffective due to the belief that a source of nitrogen for amination of the keto-acids would not be available. Prior art teachings also would not indicate that conversion of the keto-acid analogs of methionine and phenylalanine to amino acids would occur in muscle, as is taught by the present invention. However, since blood from the intestines does not go directly to the liver in this condition but rather to the systemic circulation where, presumably according to prior teachings, amination would not have occurred. The present teachings show that urea breakdown is not necessary to amination of keto-acids in body tissue, that such amination occurs in muscle tissue, and that the total effect of the amination process is the reduction of the accumulation of urea precursors in the body. Individuals suffering from the aforementioned disorders are known to be deficient in protein; in order to provide a useful treatment, as indicated in the co-pending application Ser. No. 669,589 of even date herewith, the compositions employing the keto analogs of the present invention provide for the reduction of ammonia in the bloodstream while simultaneously promoting protein synthesis.

Protein depletion may be treated by introduction of adequate protein to the diet. In instances, either economic or otherwise, where such a course proves impractical, the compositions of the present invention may be used to reduce protein requirements by diverting nitrogen precursors in the body away from urea formation (urea is excreted, resulting in bodily nitrogen loss) by combination of these precursors with keto-acid analogs of essential amino acids to form the amino acids.

It is now also known that the body's mechanisms for conserving protein can be altered, thereby enabling the body to more efficiently conserve endogenous essential amino acids. Keto-acids are thus useful not only as a nitrogen-free "source" of amino acids, but are also useful for diminishing losses of nitrogen from the body due to malnutrition, cancer, chronic infection, diabetes, surgery, trauma, or any other wasting disease or condition which causes wastage of body tissues. Treatment of these conditions in prior practice has involved the introduction into the body of amino acids through a central venous catheter, a dangerous and technically difficult invasive technique, in order to restore a positive nitrogen balance. According to the present invention, a positive nitrogen balance can be accomplished by oral or parenteral venous administration of keto-acids which reduces nitrogen wastage from the body.

SUMMARY OF THE INVENTION

The present invention provides a composition of matter and a method for promoting protein synthesis and suppressing urea formation in the human body, certain embodiments of the composition of matter and of the method being applicable to therapeutic treatment of renal disorders, to treatment of dietary protein deficiencies and to prevention of nitrogen wastage from the body. The treatment of hepatic disorders is disclosed and claimed in companion application Ser. No. 669,589.

The composition employed in practice of the present invention comprises keto-acid analogs of certain essential amino acids. Oral or intravenous administration of these keto-acids acts as a treatment for renal failure by promoting protein synthesis in the blood stream, thereby resulting in suppression of urea breakdown which correspondingly reduces the tendency of the liver to form urea. Contrary to the prior art prediction that a high urea breakdown rate would facilitate the use of keto-acids in the body, the present invention demonstrates that urea breakdown is not a necessary factor governing the effective use of the keto analogues of essential amino acids. The reduction of urea breakdown tends to reduce the net rate of urea-nitrogen appearance in the body, thus minimizing the rate of urea formation by the liver. Accordingly, renal disorders, such as uremia, may be controlled in certain instances without dialysis or as a supplement thereto.

The successful treatment of renal failure with keto-acids also occurs due to the fact that the body's mechanisms for conserving protein are altered by this introduction of keto-acids into the body. Normal metabolic pathways are altered such that leakage of nitrogen from the body's metabolic pool is reduced by keto-acid administration into the body. This alteration of metabolic processes occurs when nitrogen intake is reduced to a low level and these analogs are administered. Thus, endogenous amino acids are more efficiently reutilized in the treatment of renal failure as well as in the treatments described hereinafter for dietary protein deficiencies.

The invention is further applied to treatment of protein deficiencies by reducing protein requirements. Conversion of the keto-acid analogs of certain essential amino acids in the body suppresses urea formation by diverting nitrogenous precursors of urea away from urea formation through combination of said precursors with the keto-acids to form amino acids. Urea formed in the body is normally excreted, thereby resulting in a systematic loss of elementary protein components. Reduction of this loss of urea coupled with conversion of said nitrogenous urea precursors to available amino acids allows bodily conservation of protein without toxic effects. The "turning off" of the body's mechanisms for leaking nitrogen from the body's metabolic pool assists in maintaining nitrogen balance.

It is therefore an object of the invention to provide a composition of matter and a method for promoting protein synthesis, suppressing urea formation, and reducing nitrogen leakage from the metabolic pool in the human body.

It is another object of the invention to provide a therapeutic treatment for renal disorders and for dietary protein deficiencies.

It is a further object of the invention to administer the keto-acid analogs of certain essential amino acids to individuals suffering from renal disorders, and dietary protein deficiencies in order to mitigate the symptomatic responses of said individuals.

A still further object of the invention is the prevention of the wasting of body nitrogen during periods of low nitrogen intake or nitrogen wastage by alteration of the body's mechanisms for conserving protein.

Further objects and attendant advantages of the invention will become more readily apparent from the following detailed description of the preferred embodiments of the invention.

DESCRIPTION OF THE PREFERRED EMBODIMENTS

Figure 1A:
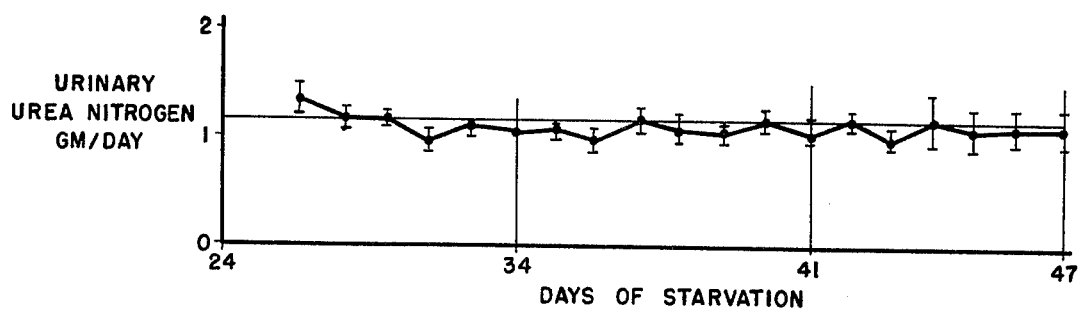
FIG. 1a is a graph illustrating the elimination of urinary urea nitrogen of a control group during starvation.

The present composition of matter and methods relative to its use generally depend, in the several embodiments thereof, on the promotion of protein synthesis and suppression of urea formation in the body. The present invention embodies the now realized need to minimize rather than accelerate the breakdown of urea in the human gut during treatment of renal failure and protein deficiency.

The invention particularly comprises therapeutic compositions including as constituents thereof the keto-acid analogs of certain essential amino acids. These compositions may be used in conjunction with other treatments effective in reducing urea breakdown in the body so as to minimize the rate of urea formation by the liver. Additionally, as hereinafter described, administration of the described keto analogues of essential amino acids effect alteration of the body's mechanisms for conserving protein and thereby prevent nitrogen loss from the body's metabolic pool.

The composition of the present invention generally comprises the keto-acid analogs of the amino acids listed in the lefthand column of Table I below, the righthand column of the Table listing the proper names for the keto-acids themselves.

Table I

| Amino Acid | Keto-Acid Analog |
|---|---|
| Valine | Alpha-ketoisovaleric acid |
| Phenylalanine | Phenylpyruvic acid |
| Methionine | Alpha-keto-gamma-methylthiobutryic acid |
| Leucine | Alpha-ketoisocaproic acid |
| Isoleucine | Alpha-keto-beta-methylvaleric acid |
| Histidine | Imidazolepyruvic acid |
| Tryptophan | Indolepyruvic acid |
| Lysine | Alpha-keto-gamma-aminocaproic acid |
| Threonine | Alpha-keto-beta-hydroxybutyric acid |

Various combinations of the keto-acids listed above may be administered either orally or parenterally as the alpha-keto acids per se or as salts thereof, preferably as the sodium or calcium salts, those individuals having a tendency to retain sodium being better treated with the calcium salts. Intravenous administration of these keto-acids may often be more effective in severe instances of renal or hepatic disease or for individuals incapable of oral ingestion of medication.

The keto-acid analog of isoleucine exists in two optical isomeric forms; these two forms of the keto-acid analog of isoleucine are interconverted in the body. The keto analogue of L-isoleucine, the naturally occurring amino acid, is dextrorotary. When administered, it is racemized in the body. Since the racemic composition of the keto analogues of L-isoleucine is considerably less expensive than the pure dextro form and has been found equally effective for the purposes of the present invention, the use of racemic alpha-keto-beta-methylvaleric acid has pronounced economic advantages.

The keto-acid analogs of the first five listed amino acids of Table I are most readily available at reasonable costs. Accordingly, the amino acids themselves of the last four listed amino acids may be used in the several embodiments of the present composition of matter. The keto-acid analogs of histidine and tryptophan are more readily available than are the keto-acid analogs of lysine and threonine, and may thus also be more commonly used in practice of the invention.

While histidine and arginine are regarded as essential amino acids based on their dietary requirement for growth of rats, these were not generally considered as essential in humans. More recent investigations, however, indicated that histidine might well be essential in treatment of uremic patients on restricted protein intake and possibly might be an essential amino acid in all human subjects, contrary to earlier beliefs. Accordingly, L-histidine or its keto analog is included as a component in the compositions of the present invention, particularly for treatment of renal disorders.

In one embodiment of the invention found to be economically attractive while retaining therapeutic viability, the keto-acid analogs or salts of the keto acid analogs of valine, phenylalanine, methionine, leucine, and isoleucine as previously listed are administered either orally or intravenously along with the amino acid for which the keto-acid analogs are not readily available at the present time, e.g., L-tryptophan, L-threonine, L-lysine, and L-histidine.

The respective mixtures of these compounds which form the several preferred embodiments of the invention, particularly those compounds used to treat renal disorders, are most often administered in four identical daily doses. Of course, the dosage of individual components of the invention can be modified if analysis of the user's blood for the corresponding amino acids reveals an abnormal balance.

In order to understand the activity of the invention in the body, careful tests on rats were conducted. It was found that isolated livers of rats perfused with 2 to 5 mM of alpha-keto isovaleric acid, alpha-keto-beta-methylvaleric acid, phenylpyruvic acid, alpha-keto-gamma-methylthiobutyric acid, or alpha-keto isocaproic acid, utilize all five compounds rapidly at the rate of 1 to 4 micro mols per minute. Glucose release and urea production were unaffected. However, there was a marked increase in release of the corresponding amino acids. Approximately 25% of the keto-acid analogs of leucine, methionine, and phenylalanine; approximately 8% of the keto-acid analog of isoleucine; and approximately 8% of the keto-acid analog of valine taken up reappeared as amino acid. Levels of critical metabolites in freeze-clamped liver were unaffected.

The keto-acid analogs of phenylalanine, valine, and isoleucine were also tested in perfused hind quarters at 2 to 8 mM. All were rapidly utilized at a rate of 2 to 4 micro mols per minute per 30 grams of muscle. The corresponding amino acids appeared in the medium in greatly increased quantities. Alanine release diminished. Thus, these five keto-acids are rapidly converted to amino acids both in rat liver and muscle both when these compounds are administered singly and when five of them are given simultaneously. Degradation also occurs and particularly to a larger extent in the keto-acid analogs of the branched chain amino acids: valine, leucine and isoleucine. Treatment with the present composition of matter has not caused keto-acids to accumulate in the blood.

As indicated above, the administered optically active keto analog of isoleucine is rapidly racemized in the body. Whether so administered as the optically active isomer or directly in racemic form, a portion thereof accumulates as alloisoleucine. It has not been established whether the L-alloisoleucine thus appearing in the blood stream serves a useful purpose. Applicant has established, however, that the alloisoleucine is not toxic, contrary to possible expectations, and furthermore that it is not incorporated into protein. This partial conversion of the administered keto analogue of isoleucine to alloisoleucine in addition to the desired isoleucine further supports the rationale for inclusion of increased quantities of the keto analog of isoleucine in the preferred compositions of the present invention. It has been established by work carried out in development of the present invention not only that desired nitrogen balance can be maintained when using the racemic keto analogue of isoleucine but also that its use in the described compositions is safe and effective in long term therapy.

Since the present invention may be practiced in the treatment of several bodily disorders in which protein synthesis and urea suppression play important therapeutic roles, it is desirable to consider these treatments individually in order to more clearly define the respective embodiments of the invention.

The following description is thus divided into subject areas relating to the bodily disorders for which the invention finds medicinal application. A discussion of the alteration of the body's mechanisms for conserving protein is also given, it being understood that this alteration produced by keto-acid administration acts to produce the effects noted in the treatment of the several disorders discussed herein.

TREATMENT OF RENAL DISORDERS

In the human body, nitrogenous waste is produced from the breakdown of proteins and amino acids. These wastes are normally excreted by the kidneys. If kidney function becomes deficient, nitrogenous wastes accumulate to toxic levels in bodily fluids, resulting in a disease known as uremia. Restriction of dietary protein reduces waste accumulation but may result in a negative nitrogen balance which progressively depletes bodily stores of protein. Exogenous protein may be supplemented (inadequately) by amino acids administered orally or parenterally. Even with such treatment the end products of nitrogen metabolism, primarily urea, continue to accumulate due in part to the breakdown of the exogenous amino acids themselves.

According to one embodiment of the invention, keto-acid analogs of valine, methionine, isoleucine, leucine, phenylalanine, histidine, tryptophan, lysine, and threonine may be administered either orally or intravenously to produce an improved symptomatic response to an individual suffering from uremia. According to the availability of these keto-acids, the amino acids L-histidine, L-tryptophan, L-lysine, and L-threonine may be used in a composition also containing alpha-ketoisovaleric acid, alpha-keto-gamma-methylthiobutyric acid, alpha-keto-beta-methylvaleric acid, alpha-ketoisocaproic acid, and phenylpyruvic acid for oral or intravenous administration to a uremic individual. It is often possible to substitute the keto-acid analog of histidine, i.e., imidazolepyruvic acid, and the keto-analog of tryptophan, i.e., indolepyruvic acid, for L-histidine and L-tryptophan respective in the composition described.

Oral administration of the keto-acid analogs of valine, methionine, isoleucine, leucine, and phenylalanine as the sodium or calcium salts and the amino acids L-histidine, L-tryptophan, L-lysine, and L-threonine, as described above, was made to uremic individuals in doses totaling 6 to 15 grams for about 17 days in concert with a minimal protein-diet. Net nitrogen intake, i.e., intake less urinary protein nitrogen, averaged 1.8 grams per day. In five severe uremics (average urea clearance being less than 2ml. per minute), serum urea nitrogen fell 40 ± 1% while urinary non-protein nitrogen averaged 2.2 grams per day. A few days after discontinuation of ingestion of the aforesaid composition, serum urea nitrogen increased.

On administration of the present composition to "terminal" uremics, i.e., individuals whose average nitrogen clearance was less than 0.4ml. per minute, serum urea nitrogen stabilized with mildly negative nitrogen balance on a net nitrogen intake of 1.2 grams.

Certain uremic individuals are unable to eat or take oral medication. Accordingly, parenteral nutrition must be provided. Previously, solutions of amino acids were administered intravenously. As previously described, however, such treatment did not prove to be effective.

According to the present invention, the keto-acid analogs of the amino acids described above may be administered intravenously in order to lower blood urea nitrogen, and therefore to reduce the severity of the uremic syndrome, by diverting nitrogenous precursors away from urea formation and by altering the body's metabolic pool. Intravenous usage of the present composition is therefore particularly suited to the treatment of individuals suffering from severe uremia.

The daily requirements of the individual keto acid analogs of the mixture are preferably supplied in the form of their sodium or calcium salts, for oral or parenteral administration; the calcium salts being preferable in most cases of renal failure owing to sodium retenion generally encountered in this condition. In the preferred practice, the prescribed total daily requirement is preferably administered divided into four identical aliquot doses. For parenteral administration, the prescribed daily requirement may be given at one time over a period of about three or four hours.

In Table II below, a practical range of the individual components of the mixture is set out, intended for administration to uremic patients of below average body weight (less than 50 kgs.) at the lower end of the disclosed range and to patients of higher than average body weight (above about 75 kgs.) at the upper end of the disclosed range. When individual idiosyncrasies are encountered, such as an abnormal balance of the corresponding amino acids in the patient's blood, the dosage of the individual components of the administered mixture can be modified.

Compositions falling within the ranges set out in Table II may be employed in oral as well as in parenteral administration. It has been observed that alpha-keto-isocaproic acid particularly is partially degraded by the intestines and furthermore that all three of the branched-chain keto acids are in fact partially degraded and relatively inefficiently aminated in the liver. Since the liver drains the blood from the intestines, it appears that higher quantities of these branched-chain keto analogs should preferably be employed in oral therapy than in intravenous administration, as for example, in amounts approaching the higher end of the range set out in Table II and in the order of up to about triple the amount of the other two keto analogues of the mixture.

It will be observed that the respective quantities of the components in the mixture tabulated below are based on using approximately twice the equivalent quantities of the branched chain amino acid analogs (of valine, leucine and isoleucine) as compared to the quantities of the keto analogs of phenylalanine and methionine.

TABLE II

| MINIMUM DAILY DOSAGE FOR INTRAVENOUS ADMINISTRATION | |
|---|---|
| Quantity | Substance |
| 1.5 – 2.5 grams | phenylpyruvic acid; sodium or calcium salt |
| 2.0 – 4.0 grams | alpha-ketoisovaleric acid; sodium or calcium salt |
| 3.0 – 5.0 grams | alpha-ketoisocaproic acid; sodium or calcium salt |
| 2.5 – 3.5 grams | alpha-keto-beta-methylvaleric acid; sodium or calcium salt |
| 1.5 – 2.5 grams | alpha-keto-gamma-methylthiobutyric acid; sodium or calcium salt |
| ~0.54 gram | L-histidine |
| ~0.8 gram | L-lysine monohydrochloride or acetate |
| ~0.5 gram | L-threonine |
| ~0.25 gram | L-tryptophan |

A solution of the composition is prepared by first dissolving the sodium salt of phenylpyruvic acid in 50 ml of distilled water with the aid of warming, and then adding the remaining components of the mixture to the resulting solution. Solution of all the substances being thus accomplished, the solution is sterilized by millipore filtration, and tested for sterility and pyrogenicity. The solution is frozen until use. When used, the solution is thawed to room temperature and diluted to 250 ml. with sterile, pyrogen-free water.

The isotonic solution thereby resulting has a neutral pH and is satisfactory for intravenous use. The solution is stable for at least 8 hours (and longer) at room temperature. Intravenous administration of the solution may be accomplished over a three to four hour period in a bottle protected by aluminum foil from light. In certain solutions, more than one infusion may be given daily.

The effect of uremia treatment with the present composition of matter may be clearly seen from the data presented in Table III. The mixture of substances orally employed and denoted in Table III as KA were, as previously described, the alpha-keto-acid analogs of valine, leucine, methionine, phenylalanine, and isoleucine along with L-histidine, L-tryptophan, L-lysine, and L-threonine.

jects could not normally be managed except by dialysis. Administration of the present composition generally enables maintenance of these subjects with low blood urea and positive nitrogen balance, the subjects being essentially free of uremic symptoms without the need for dialysis.

In individuals wherein the renal function has ceased to exist, treatment with the present composition allows less frequent need for dialysis. Individuals requiring dialysis twice per week often need dialysis only once a month when treated according to the present invention. In such a situation, only a minimal rise in blood urea is experienced. The lack of a renal function in such individuals is confirmed by the progressive rise in blood creatinine (which does not produce symptoms).

Previously reported in the literature was a position taken by certain investigators that a high blood urea level would be an essential prerequisite in using keto analogs of certain of the essential amino acids in chronic renal failure, when administered in association with a

TABLE III

| | | | NITROGEN METABOLISM IN UREMIC PATIENTS DURING AND AFTER ADMINISTRATION OF KETOACIDS (KA) | | | |
|---|---|---|---|---|---|---|
| Subject | Days | Rx | Net N Intake g/day | Urea N Appearance g/day | N Balance g/day | Urea Clearance ml/min |
| A | 1–8 | KA[1] | 0.99±0.27 | 1.07±0.49 | | 0.69+0.06 |
| | 9–15 | KA | 1.68±0.11 | −0.37±0.23 | +0.87±0.26 | 0.69±0.14 |
| | 16–20 | None | 1.18±0.01 | 1.30±0.32 | −0.95±0.38 | 1.58±0.25 |
| | Change[2] | | −0.50±0.12[3] | +1.67±0.39[3] | −1.82±0.46[3] | +0.89±0.29[3] |
| B | 1–8 | KA[1] | 2.47±0.17 | 2.32±0.16 | | 1.64±0.06 |
| | 9–15 | KA | 1.84 ±0.30 | 0.04 ±0.11 | +0.36±0.22 | 1.44±0.07 |
| | 16–20 | None | 1.53±0.29 | 3.09±0.05 | −2.95±0.34 | 1.62±0.01 |
| | Change[2] | | −0.31±0.42 | +3.05+0.12[3] | −3.31±0.40[3] | +0.18±0.08[4] |
| C | 1–7 | KA | 0.95±0.27 | 2.60±0.84 | −2.96±0.52 | 5.35±0.30 |
| | 8–18 | KA | 3.01±0.14 | 2.44±0.11 | −0.90±0.26 | 5.82±0.74 |
| | 19–23 | None | 2.89±0.11 | 3.18±0.29 | −1.88±0.37 | 5.01±0.56 |
| | Change[2] | | −0.15±0.18 | +0.74±0.31[3] | −0.98±0.45[4] | −0.78±1.31 |
| D | 1–9 | KA | 1.18±0.19 | 0.58±0.12 | −0.62±0.28 | 1.05±0.12 |
| | 10–17 | KA | 1.66±0.06 | 0.48±0.01 | +0.03±0.12 | 1.31±0.08 |
| | 18–21 | None | 1.44±0.16 | 1.63±0.01 | −0.91±0.25 | 1.17±0.13 |
| | Change[2] | | −0.22±0.17 | +1.15±0.04[3] | −0.94±0.28[3] | −0.17±0.15 |
| E | 1–9 | KA | 2.09±0.17 | 0.95±0.06 | −0.01±0.26 | 1.09±0.02 |
| | 10–18 | KA | 2.23 ±0.01 | 0.61±0.10 | +0.89±0.15 | 1.10±0.04 |
| | 19–24 | None | 1.68±0.07 | 1.73±0.07 | −0.72±0.08 | 1.19±0.06 |
| | Change[2] | | −0.55±0.08[3] | +1.12±0.12[3] | −1.61±0.17[3] | +0.09±0.09 |

[1]Ketoacid dosage increased gradually to final value during this period.
[2]Difference between second period of ketoacid thereapy and final control period.
[3]Difference is significant (P < 0.02).
[4]Difference is significant (P < 0.05).

Table III provides data relative to the oral administration of the composition described above in five patients with renal failure who were studied during two periods of treatment with the present composition while on a low protein diet and also during a subsequent control period during which the present composition was not administered. The column of Table III denoted as "Urea N Appearance" refers to the rate at which urea is being released into body fluids.

In subjects A through E, the rate at which urea was being formed increased on discontinuation of the present composition. As seen in the column denoted as "N balance", nitrogen balance became more negative upon discontinuation of the present composition. As can be directly determined from the data shown, a substantial increase in the final steady level of blood urea can be anticipated when administration of the present composition is discontinued. Thus, in the absence of the present composition, these subjects A through E could be expected to become substantially more ill.

Referring again to Table III in the column denoted as "Urea clearance", it is seen that the rate of urea clearance for subjects A through E is so low that said subprotein-restricted diet. These investigators indicated that if the blood urea level fell it would be necessary to add non-essential nitrogen in the treatment or to give up this form of treatment therapy and return to the heretofore conventional low protein diet. Contrary to the conclusions heretofore advanced, applicant has found that in fact blood urea can be maintained at very low levels for long periods with the use of the compositions of the present invention in chronic renal failure and furthermore urea degradation for reutilization of the released urea nitrogen was not a prerequisite for the efficaceous use of the proposed keto analogs of the essential amino acids. In fact, it was found in the development of the present invention, that subjects having high blood urea levels, could not be treated as effectively with the keto analog containing compositions as those having lower blood urea levels. This is illustrated by the data reported in Table IV.

TABLE IV
NITROGEN METABOLISM IN FOUR PATIENTS DURING ADMINISTRATION OF KETOACIDS IN THE PRESENCE OF HIGH BLOOD UREA LEVELS

| Subject | Serum urea N mg/100 ml | Days of Keto-acid therapy | Net N Intake g/day | urea N appearance g/day | N balance g/day | Urea clearance g/day |
|---|---|---|---|---|---|---|
| F | 168 | 25 | 1.04 ±0.21 | 0.03 ±0.20 | −1.74 ±0.13 | 0.32 ±0.02 |
| G | 201 | 8 | 1.52 ±0.11 | 0.93 ±0.40 | −1.56 ±0.47 | 0.42 ±0.02 |
| H | 156 | 15 | 0.89 ±0.10 | 1.13 ±0.15 | −2.16 ±0.57 | 0.52 ±0.01 |
| I | 174 | 5 | 1.57 ±0.15 | 2.55 ±0.23 | −5.43 ±0.26 | 1.47 ±0.10 |

The data provided in Table IV indicate that these subjects F through I, having high urea breakdown rates are less prone to effective therapy employing keto analogues of the essential amino acids. These data show the fallacy of the prior prediction, based on studies with keto acids individually administered, that the use of keto acids would be facilitated by high urea breakdown rates.

Contrary to the earlier predictions, elimination of urea breakdown in subjects F through I would facilitate their response to treatment according to the invention. The information provided by Tables III and IV substantiate that treatment according to the invention reduces the tendency of the liver to form urea due to reduction of urea breakdown in the body. The net rate of urea-nitrogen appearance is thereby reduced. It can therefore be seen that administration of the present composition in treatment according to the invention may be effectively used also in combination with additional conventional treatment to reduce urea breakdown in the body, thereby to minimize the rate of urea formation by the liver. Among such known treatments applied to reduce urea breakdown in the gut is the administration of certain antibiotics.

TREATMENT OF PROTEIN DEPLETION

Protein depletion usually occurs due to the low availability of dietary protein or increased nitrogen loss. The object of the embodiment of the invention now described is to reduce the exogenous protein requirement of an individual in such a manner that protein is actually conserved in the body. Generally, the composition of matter employed in this embodiment of the invention is that composition described previously relative to the treatment of renal disorders, except that L-histidine or the keto-acid analog thereof may in certain instances be omitted. The composition would then comprise the keto-acid analogs of valine, leucine, isoleucine, methionine, phenylalanine, lysine, threonine, and tryptophan. The keto-acid analog of histidine may also be used as a component of the mixture. Alternatively, and due to practical availability, the mixture may be formed using the amino acids L-lysine, L-threonine, L-tryptophan, and L-histidine in place of the keto-acid analogs thereof. This mixture could be given orally or intravenously.

It can be shown that administration of this embodiment of the present composition of matter diverts nitrogenous precursors of urea away from urea formation due to the combination of said precursors with keto-acids to form amino acids. This treatment leads to an alteration of the body's metabolic machinery such that urea formation, and therefore protein requirement, is reduced even for a period of time after treatment has been discontinued. Thus, individuals so treated are made more capable of conserving protein as a result of treatment according to the invention. Although nitrogen may still be lost from the body, the body's ability to conserve protein is increased, thereby reducing exogenous protein requirements.

ALTERATION OF THE BODY'S MECHANISMS FOR CONSERVING PROTEIN

Administration of keto-acids into the body in the treatment of the several disorders described hereinabove, when used in concert with low protein diets, causes a substantial reduction in nitrogen excretion measured as urea, thereby indicating that the body's mechanisms for conserving protein are altered to enable the body to more efficiently conserve protein.

Thus, the mechanism by which keto-acids promote nitrogen conservation in the disorder described herein is not simply by means of the conversion of the keto-acids to essential amino acids. While the administration of keto-acids do facilitate nitrogen conservation directly by restoring carbon skeletons lost by degradation, metabolic pathways are also altered which allow endogenous keto-acids to be more efficiently re-utilized in the body.

Figure 1B:
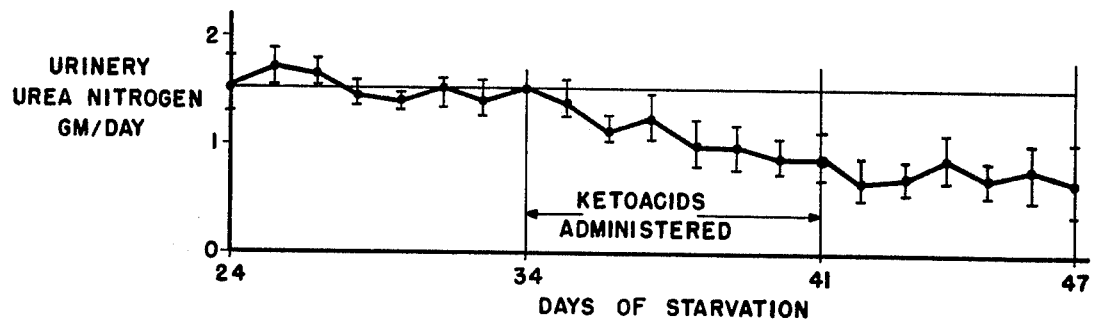
FIG. 1b is a graph illustrating the elimination of urinary urea nitrogen of a group of patients during starvation having keto-acid analogs of essential amino acids administered for a one week period.
Figure 2:
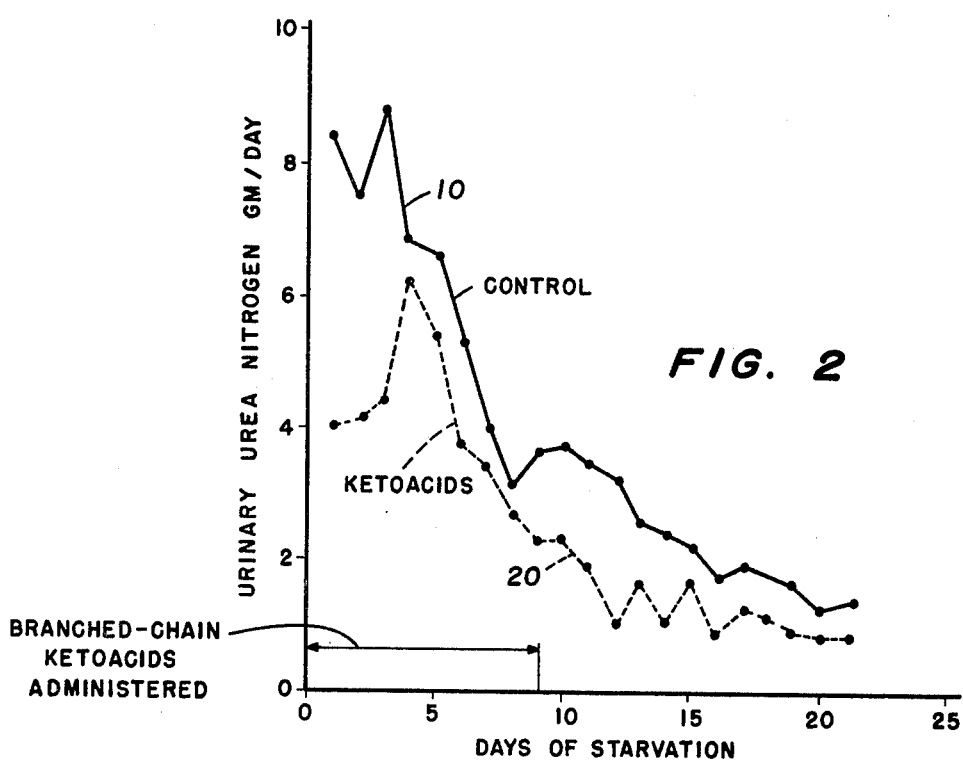
FIG. 2 is a graph illustrating the elimination of urinary urea nitrogen of an individual during two periods of starvation, during one of which a mixture of branched-chain keto-acids was administered daily for the first week.
Figure 3:
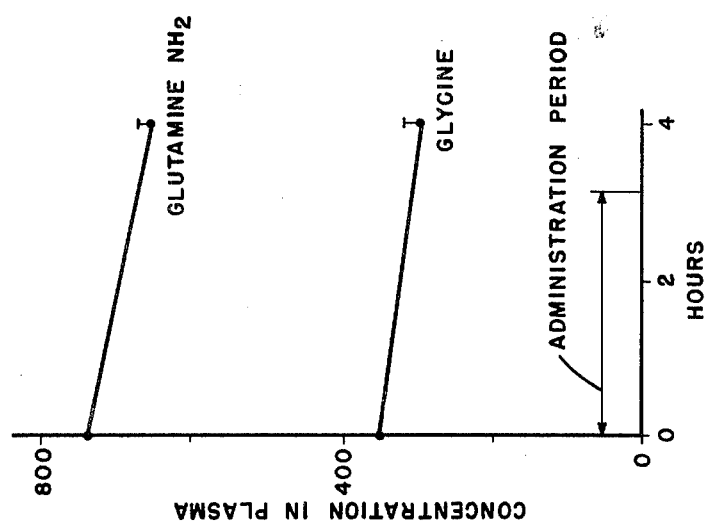
FIGS. 3a, 3b and 3c are graphs illustrating the concentration of amino acids in the blood of the group of patients undergoing the treatment indicated in FIG. 1b.

Alteration of these nitrogen-sparing mechanisms in normal subjects are shown by the data presented in FIGS. 1 through 3. Two groups of obese individuals undergoing total starvation for the number of days indicated are compared on the horizontal axes of FIGS. 1a and 1b, the groups of FIG. 1a being a control group and the group of FIG. 1b undergoing keto-acids administration as will be described hereinafter. Urinary urea nitrogen was measured in the two groups during the period extending between the third and seventh weeks of starvation.

In the control group of FIG. 1a, urinary urea elimination can be seen to be at a low but constant level during this period. The group of FIG. 1b exhibits essentially the same urinary urea elimination response up until the 34th day of starvation, at which time they were given a mixture of the keto-acid analogs of valine, leucine, methionine, isoleucine, and phenylalanine (as the sodium salts thereof) and also the amino acids lysine, tryptophan, threonine, and histidine, in amounts equivalent to one Rose unit of each component of the mixture. This mixture was administered each day through the 41st day.

As can be readily seen, urinary urea falls progressively during the period of keto-acid administration. It can also be seen that urinary urea remains low and is even further reduced during a period of time following administration of the keto-acid mixture. Thus, keto-acid administration lowers body nitrogen losses both during and after introduction into the body, thereby indicating that the body's mechanisms for conserving protein are altered by such administration.

FIG. 2 illustrates the treatment of an individual from the beginning of starvation; line 10 indicates treatment during a control fast and line 20 indicates treatment by the administration of only the branched-chain keto-acid analogs, i.e., the keto-acids analogs of valine, leucine, and isoleucine. These keto-acids in equimolar amounts were administered each day from the first day through the eighth day of the period, one to four grams per day of each acid being preferably administered. Typically, five grams of the composition (1.3 grams of each acid) was administered. As can be seen urinary urea is much lower, even during the first day for the period of starvation in which the patient received the keto-acids.

After discontinuation of the keto-acids, urinary urea is still substantially lower than during the control period. Thus, nitrogen -sparing is immediately induced in starving individuals and persists even after the keto-acids have been metabolized. These branched-chain keto-acid analogs are thereby seen to cause nitrogen sparing in starvation even when used alone.

Figure 3B:
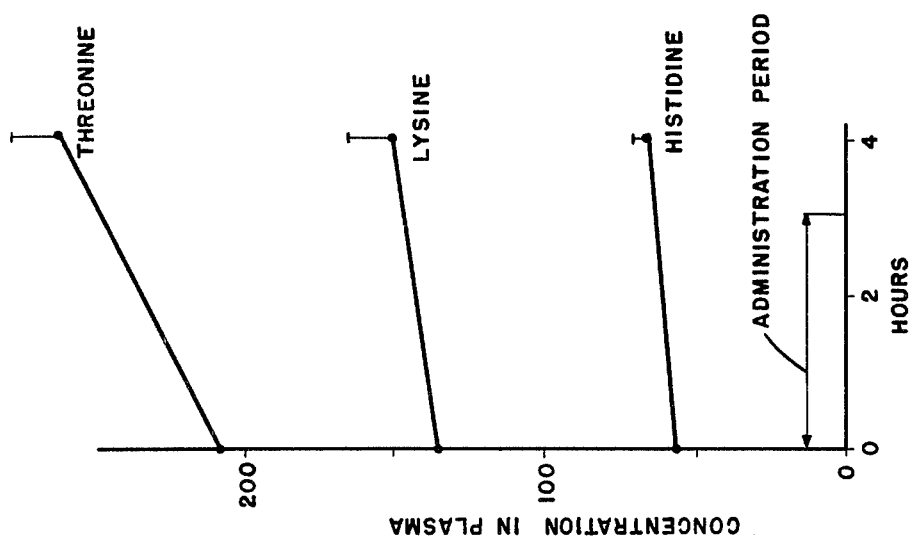
Figure 3A:
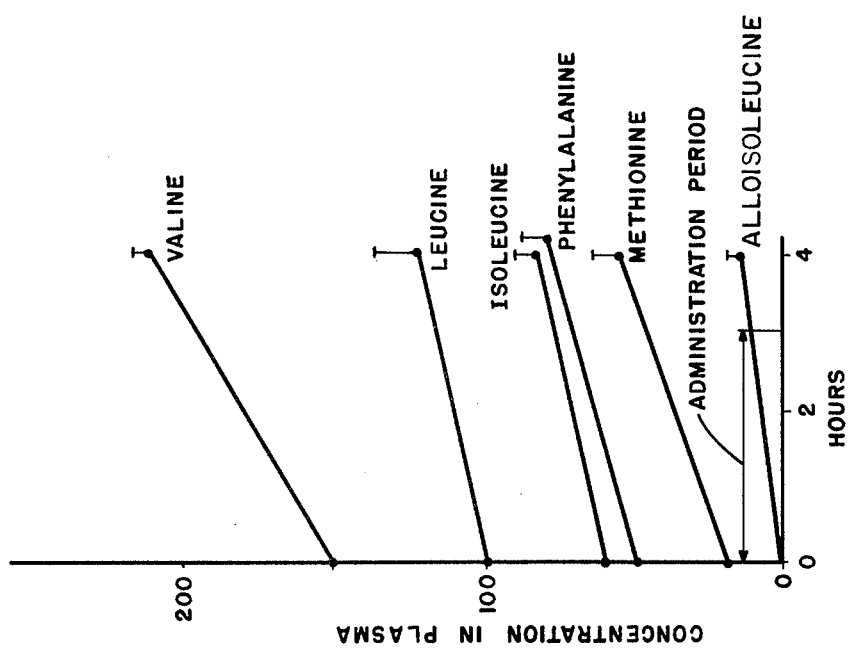

FIGS. 3a, 3b and 3c relate to the group of patients studied in FIG. 1b and show the average change in amino acid concentration in plasma during infusion of the keto-acid mixture. As seen in FIG. 3a, the amino acids corresponding to the keto-acids administered all increase in concentration. The rapid appearance of the amino acids corresponding to the infused keto-acid analogs shows that the keto acids become rapidly aminated in the body. FIG. 3b shows that the amino acids present in the mixture administered did not increase in concentration any more than did the amino acids corresponding to the infused keto acids.

FIG. 3c illustrates the fall in whole blood glutamine and glycine, thereby indicating that other amino acids are giving up their nitrogen through reaction with the keto acids to form the amino acids corresponding to said keto acids.

The data thus presented show that the body's mechanisms for conserving protein are altered by the administration of keto-acid analogs of essential amino acids into the body. It is thus indicated that protein depletion is not necessarily best corrected by administration of protein or amino acids. Protein or amino acids administration increases nitrogen losses and must be given in large quantities to counter these losses. A positive nitrogen balance is thus difficult to achieve. Reduction of nitrogen losses from the body is therefore desirable and is desirable not only in instances of malnutrition but also in wasting diseases or conditions such as cancer, diabetes, chronic infection, burns, surgery, trauma, or other conditions characterized by tissue wastage.

Nitrogen balance is restored by oral or parenteral administration of the keto-acid analogs of essential amino acids by "turning off" nitrogen wastage from the body. As long as low nitrogen intake is maintained, suppression of nitrogen leakage from the body's metabolic pool occurs.

The mechanism by which nitrogen is conserved is likely accomplished by diminution of certain amino acids in the blood, particularly alanine. The concentration of alanine is reduced by reaction in muscle tissue between the keto-acid analogs (particularly those of valine, leucine, and isoleucine) with alanine, this reduction in alanine concentration causing reduced production of urea in the liver.

The keto-acid analogs described herein are known substances. Although other methods of preparing compounds of this type are well known, a relatively inexpensive method comprises reaction of diethyloxylate with the ethyl ester of the next lowest homologous organic acid (of the desired keto acid) in the presence of sodium ethoxide and subsequently hydrolyzing the resulting product to yield the keto acid. The predicted bulk price for the keto analogs is about half of that of the corresponding essential amino acids, affording economic advantages in addition to those already set out above.

What is claimed is:

1. A composition capable of promoting protein synthesis and conserving nitrogen in a patient in need thereof, said composition being in the form of a mixture adapted for oral or parenteral administration to subjects on a protein-restricted diet, said composition consisting essentially of effective quantities of the keto-acid analogs of the branched-chain essential amino acids valine, leucine and isoleucine.

2. A composition for treatment of uremia resulting from renal disorders comprising a mixture in form for oral or parenteral administration to subjects on a protein-restricted diet, said composition consisting essentially of the components in the following ranges of proportions by weight:

1.5 – 2.5 parts sodium or calcium phenylpyruvate;
2.0 – 4.0 parts sodium or calcium alpha-keto isovalerate;
3.0 – 5.0 parts sodium or calcium alpha-keto-isocaproate;
2.5 – 3.5 parts sodium or calcium alpha-keto-methylvalerate;
1.5 – 2.5 parts sodium or calcium alpha-keto-gamma methyl-thiobutyrate;
about 0.54 parts of L-histidine;
about 0.8 parts of L-lysine hydrochloride;
about 0.5 parts of L-threonine;
about 0.25 parts of L-tryptophan.

3. A method for promoting protein synthesis and conserving nitrogen in a non-uremic patient in need thereof comprising orally or parenterally administering in effective dosage to subjects on a protein-restricted diet a composition substantially devoid of non-essential amino acid in free form; said composition comprising effective quantities of the essential amino acids valine, phenylalanine, methionine, leucine, isoleucine, tryptophan, lysine and threonine, or the keto analogs of said essential amino acids, at least the five essential amino acids valine, leucine, isoleucine, phenylalanine and methionine being present in the composition as the respective keto analogs thereof, said keto analogs being present in the form of the alpha-keto acids per se or salts of the alpha-keto acids.

4. A method as defined in claim 3 wherein said composition also contains the amino acid histidine or a keto analog thereof.

5. A method as defined in claim 4 wherein said composition contains in amino acid form: L-histidine, L-lysine hydrochloride or acetate, L-threonine and L-tryptophan.

6. A method as defined in claim 4 wherein histidine is present in said composition in the form of a salt of its alpha keto acid analog.

7. A method as defined in claim 3 wherein said keto analogs in the composition are present as calcium or sodium salts of the keto acids.

8. A method as defined in claim 3 wherein the salts of the five recited keto analogs are present in said composition in amounts to afford dosages constituting at least the minimum daily requirement of the corresponding essential amino acid.

9. A method as defined in claim 3 wherein the quantities of the salts of the keto acids of valine, leucine and isoleucine are each present in said composition in approximately two to three times that of the salts of phenylalanine and methionine.

10. A method as defined in claim 3 wherein tryptophan is present in said composition in the form of a salt of its alpha keto acid analog.

11. A method as defined in claim 3 wherein the five recited keto analogs are present as salts in the weight proportions: 2 to 4 parts valine analog, 3 to 5 parts leucine analog, 2.5 to 3.5 parts isoleucine analog, 1.5 to 2.5 parts each of the analogs of methionine and phenylalanine.

12. A method as defined in claim 11 wherein said composition is parenterally administered as a sterilized isotonic aqueous solution.

13. A method for treatment of uremia resulting from renal disorders which comprises oral or parenteral administration in effective dosage to a subject on a diet of restricted amounts of protein, a therapeutic composition substantially devoid of non-essential amino acid; said composition consisting essentially of the components in the following ranges of proportions by weight:
 1.5 – 2.5 parts sodium or calcium phenylpyruvate;
 2.0 – 4.0 parts sodium or calcium alpha-keto-isovalerate;
 3.0 – 5.0 parts sodium or calcium alpha-keto-isocaproate;
 2.5 – 3.5 parts sodium or calcium alpha-keto-betamethyl-valerate;
 1.5 – 2.5 parts sodium or calcium alpha-keto-gammathiobutyrate;
 about 0.54 parts of L-histidine;
 about 0.8 parts of L-lysine hydrochloride;
 about 0.5 parts of L-threonine;
 about 0.25 parts of L-trptophan.

14. The method as defined in claim 13 wherein the defined composition is intravenously administered to patients suffering severe uremic syndrome for the purpoe of diminishing the rate of urea formation in the liver of such patients.

15. The method as defined in claim 13 wherein said composition is orally administered.

16. A method for promoting protein synthesis which comprises orally or parenterally administering to a non-uremic subject in need of such protein synthesis an effective amount of a mixture of the alpha-keto-acid analogs of valine, leucine, isoleucine, methionine and phenylalanine in amounts of at least one to one and a half times the minimum daily requirements of the corresponding amino acid, said mixture being free of non-essential amino acid.

17. The method of conserving protein in the human body and reducing exogenous protein requirement in a non-uremic subject having protein deficiency as a result of low availability of dietary protein or increased loss of nitrogen, which method comprises oral or parenteral administration to such subject a mixture of the eight essential amino acids: valine, leucine, isoleucine, methionine, phenylalanine, lysine, threonine and tryptophan; of which amino acids at least the first five named are administered in the form of salts of the alpha-keto acid analogs of such amino acids.

18. A method for promoting protein synthesis and conserving nitrogen in a patient in need thereof comprising orally or parenterally administering in effective dosage to subjects on a protein-restricted diet a composition consisting essentially of effective quantities of the keto-acid analogs of the branched-chain essential amino acids valine, leucine and isoleucine.

* * * * *